United States Patent [19]

Azizian et al.

[11] Patent Number: 5,124,257
[45] Date of Patent: Jun. 23, 1992

[54] METHOD FOR PREPARING L-ALANINE

[76] Inventors: Asmik G. Azizian, ulitsa Estonakan,3,kv.33; Artur A. Ambartsumian, Noragavit,6 ulitsa,3; Maritsa A. Ananikian, ulitsa Tikhogo Dona,27,kv.168; Shavarsh M. Kocharian, ulitsa Paroniana, 11, kv.4, all of Erevan, U.S.S.R.

[21] Appl. No.: 449,878
[22] PCT Filed: Apr. 25, 1989
[86] PCT No.: PCT/SU89/00111
    § 371 Date: Dec. 22, 1989
    § 102(e) Date: Dec. 22, 1989
[87] PCT Pub. No.: WO89/10408
    PCT Pub. Date: Nov. 2, 1989

[30] Foreign Application Priority Data

Apr. 26, 1988 [SU] U.S.S.R. .................. 4408234

[51] Int. Cl.$^5$ .............. C12P 13/06; C12N 1/20; C12N 1/00
[52] U.S. Cl. .............. 435/116; 435/252.32; 435/840; 435/843
[58] Field of Search .................. 435/116, 252.32, 840, 435/843

[56] References Cited

FOREIGN PATENT DOCUMENTS

| 310949 | 4/1989 | European Pat. Off. | 435/116 |
| 1038489 | 6/1973 | Japan | 435/116 |
| 7319953 | 3/1976 | Japan | 435/116 |

OTHER PUBLICATIONS

Zaitseva et al., Biological Abstracts, vol. 79(12), #103932.
Kase et al., Biological Abstracts, vol. 64(3), #14198.
Linde et al., Biological Abstracts, vol. 62(1), #1779.

Primary Examiner—Ronald W. Griffin
Assistant Examiner—Pamela S. Webber
Attorney, Agent, or Firm—Burgess, Ryan & Wayne

[57] ABSTRACT

A method for preparing L-alanine comprising culturing of mutants of microorganisms of the genus Brevibacterium or Corynebacterium requiring D-alanine for their growth on a nutrient medium containing assimilable sources of carbon, nitrogen, inorganic salts and stimulants of growth of the microorganisms until accumulation of L-alanine in the cultural liquid and the subsequent isolation of said product.

6 Claims, No Drawings

METHOD FOR PREPARING L-ALANINE

BACKGROUND OF THE INVENTION (1) Field of the Invention

The present invention relates to the microbiological industry, more particularly to methods of preparing aminoacids and, more specifically, to a fermentation method for preparing L-alanine (2) Background of the Related Art Known in the art are methods for preparing L-alanine by way of transformation from aspartic acid using immobilized cells of microorganisms possessing a $\beta$-decarboxylase activity (U.S. Pat. No. 3,898,128).

Such known methods are multi-stage ones which is associated with the necessity of producing, for example, in the first stage of the process, L-aspartic acid from ammonium fumarate by transformation with the use of aspartase and, in the second stage of the process - transformation of the resulting L-aspartic acid into L-alanine by means of L-aspartate-$\beta$-decarboxylase (Progress in Industrial Microbiology, v. 24, 1986, Tokyo, J. Chibata, T.Tosa, T. Kakimoto "Alanine", p. 224–232).

Known in the art is a method for recovering L-alanine for a racemic mixture, wherein D,L-alanine is subjected to acetylation and then, by means of an enzyme - aminoacylase, acetyl-L-alanine is selectively hydrolyzed to give L-alanine. Afterwards, L-alanine is separated from acetyl-D-alanine (U.S. Pat. No. 3,386,888).

This is a multi-stage process necessitating preparation of intermediate D,L-alanine, acetyl-D,L-alanine, aminoacylase enzyme, thus making the process more complicated and expensive.

SUMMARY OF THE INVENTION

The present invention, by using a novel type of mutants of microorganisms, provides a method for preparing L-alanine which would make it possible to simplify the process for obtaining the desired product in a commercially acceptable yield of the desired product in a culture liquid.

This problem is solved by a method for preparing L-alanine which utilizes culturing of microorganisms of the genus Brevibacterium and Corynebacterium on a nutrient medium containing assimilable sources of carbon, nitrogen, inorganic salts and organic compounds, stimulating growth of the microorganisms till accumulation of L-alanine in the cultural liquid and a subsequent recovery of the desired product. In accordance with the present invention, as the microorganisms use is made of mutants of microorganisms of the genus Brevibacterium and needing D-alanine for their growth.

Owing to the present invention it is now possible to prepare optically pure L-alanine in a culture liquid, avoiding previously indespensable stages associated with the recovery of L-alanine from a racemic mixture, the desired product content in the cultural liquid reaching 28 g/l.

According to the present invention, it is advisable to use the mutants of microorganisms of the species of *Brevibacterium flavum* deposited at the Vsesojuzny Nauchno-Issledovatel'sky Institut Genetiki i Selektsii Promyshlennykh Mikroorganizmov (VNIIGenetika), Moscow, Dorozhny proezd, 1 (All-Union Research Institute of Genetics and Selection of Industrial Microorganisms/VNIIGenetika/), the strain *Brevibacterium flavum* AA1 registered under No. B-3061 on Apr. 5, 1984; the strain *Brevibacterium flavum* AA2 registered under No. B-3062 on Apr. 5, 1984.

For a further increase of the content of the desired product in the culture liquid (reaching 44/g/l), according to the present invention it is advisable that use be made of the mutants of microorganisms of the genus Brevibacterium resistant against D, L-$\alpha$aminobutyric acid.

According to the present invention, it is desirable to use mutants of microorganisms of the species *Brevibacterium flavum* deposited at the Vsesojuzny Nauchno-Issledovatel'sky Institut Genetiki i Selektsii Promyshlennykh Mikroorganizmov (VNIIGenetika):

the strain *Brevibacterium flavum* AA5 registered under No. B-3991 on Apr. 1, 1987;

the strain *Brevibacterium flavum* AA6 registered under No. B-3992 on Apr. 1, 1987.

Furthermore, it is desirable, in accordance with the present invention, to use mutants of microorganisms of the species *Corynebacterium glutaminicum* deposited at the Vsesojuzny NauchnoIssledovatel'sky Institut Genetiki i Selektsii Promyshlennykh Microorganizmov (VNIIGenetika):

the strain *Corynebacterium glutaminicum* AA41 registered under No. B-3321 on Mar. 25, 1985;

the strain *Corynebacterium glutaminicum* AA11 registered under No. B-3323 on Mar. 25, 1985.

Further objects and advantages of the present invention will now become more fully apparent from the following detailed description of the method for preparing L-alanine and specific examples illustrating particular embodiments of this method.

BEST MODE FOR CARRYING OUT THE INVENTION

The method for preparing L-alanine according to the present invention is based on the use of microorganisms producing L-alanine and cultured in a nutrient medium.

According to the present invention, use is made of mutants of microorganisms of the genus Brevibacterium and Corynebacterium needing D-alanine for their growth. Particular examples of such microorganisms are the strain—producer of L-alanine—*Brevibacterium flavum* AA1 deposited at the Vsesojuzyn NauchnoIssledovatelsky Institut Genetiki i Selektsii Promyshlennykh Mikroorganizmov (VNIIGenetika) and registered under No. B-3061 on Apr. 5, 1984;

the strain—producer of L-alanine—*Brevibacterium flavum* AA2 deposited at the Vsesojuzny Nauchno-Issledovatelsky Institut Genetiki i Selektsii Promyshlennykh Mikroorganizmov (VNIIGenetika) and registered under No. B-3062 on Apr. 5, 1984;

the strain producer of L-alanine—*Corynebacterium glutaminicum* AA41 deposited at Vsesojuzny Nauchno-Issledovatelsky Institut Genetiki i Selektsii Promyshlennykh Microorganizmov (VNIIGenetika) and registered under No. B-3321 on Mar. 25, 1985;

and the strain—producer of L-alanine—*Corynebacterium glutaminicum* deposited at the Vsesojuzny Nauchno-Issledovatelsky Institut Genetiki i Selektsii Promyshlennykh Mikroorganizmov (VNIIGenetika) and registered under No. B-3323 on Mar. 25, 1985.

In the method according to the present invention use can also be made of mutants of microorganisms of the genus Brevibacterium needing D-alanine and resistant against D,L-$\alpha$-aminobutyric acid. Examples of such microorganisms are the strains producing L-alanine-*Brevibacterium flavum* AA5 or *Brevibacterium flavum*

AA6 deposited at the Vsesojuzny Nauchno-Issledovatelsky Institut Genetiki i Selektsii Promyshlennykh Mikroorganizmov (VNIIGenetika) and registered respectively under Nos. B-3991, B-3992 on Apr. 1, 1987.

Mutations of auxotrophicity in respect to D-alanine can be induced by treatment of the microorganisms by any conventional procedure (for example, with N-methyl-N'-nitro-N-nitrosoguanidine or by UV irradiation). Mutations of resistance in relation to D,L-α-aminobutyric acid can be either spontaneous or induced as a result of treatment of the microorganisms by any conventional method. The combination, in the genome of the microorganisms, of the mutation of resistance against D,L-α-aminobutyric acid and the mutation of auxotrophicity relative to D-alanine can be effected in any sequence.

As for the parent strains for the selection of mutants necessitating D-alanine use can be made of any natural microorganisms producing alanine in the form of a racemate. The abovementioned novel strains *Brevibacterium flavum* AA1, *Brevibacterium flavum* AA2, *Brevibacterium flavum* AA6, and *Brevibacterium flavum* AA5 were obtained by methods of genetic engineering from the strain *Brevibacterium flavum* ATCC 14067 deposited at the Vsesojuzny Nauchno-Issledovatelsky Institut Genetiki i Selektsii Promyshlennykh Mikroorganizmov (VNIIGenetika) and registered under No. B-42 on Jan. 16, 1969.

The above-mentioned novel strains *Corynebacterium glutamicum* AA41 and *Corynebacterium glutamicum* AA11 have been produced by methods of genetic selection from the well-known strain *Corynebacterium glutamicum* ATCC 13032 deposited at the Vsesojuzny Nauchno-Issledovatelsky Institut Genetiki Selektsii Promyshlennykh Microorganizmov (VNIIGenetika) and registered under No. B-41 on Jan. 16, 1969.

However, as the parent strains for selection of the microorganisms employed in the method according to the present invention or the mutants necessitating D-alanine and possibly resistant against D,L-α-aminobutyric acid use can be made of any strains of microorganisms pertaining to the genus *Brevibacterium* or to the genus *Corynebacterium*.

The strains AA1, AA2, AA41, AA11 do not differ, in their characteristics (except for the auxotrophicity relative to D-alanine and L-alanine producing capacity), from the parental strains *Brevibacterium flavum* ATCC 14067 and *Corynebacterium glutaminicum* ATCC 13032, respectively.

The strains producing L-alanine according to the present invention—*Brevibacterium flavum* AA1 and *Brevibacterium flavum* AA2 have the following morphological-and-cultural and physiological and-biochemical features.

Cells are oval, slightly extending, immobile, non-sporiferous, gram-positive. Colonies on a meat-peptone agar after 48 hours of incubation are round with a smooth and, less frequently, slightly rough surface, yellow, reach 2 mm in diameter.

Facultative anaerobics. Do not liquify gelatin. Ferment glucose and saccharose. Assimilate ammonium nitrogen. The growth optimum at 30°–32° C. and at a pH of 7.2–7.8. Necessitate biotin and thiamine for their growth on minimal media.

The preparation of the strain *Brevibacterium flavum* AA1 and the strain *Brevibacterium flavum* AA2 is effected in the following manner:

The strain ATCC 14067 is grown in meat-peptone broth at the temperature of 30° C. under aeration till the titre of $10^9$ cells/ml is obtained. The cells are rinsed to remove the meat-peptone broth by centrifugation and resuspended in a citrate buffer (kpH=5.5). To the resulting suspension N-methyl-N-nitro-N-nitrosoguanidine is added to the final concentration of 300 μg/ml, incubated under aeration of 20 minutes at 30° C. Then the cells are rinsed to remove the mutagene by means of a cooled meat-peptone broth, subjected to incubation under aeration for 18 hours at the temperature of 30° C. and then inoculated onto the surface of a meat-peptone broth medium containing 2% by weight of agar-agar. The colonies grown on this medium are tested, after 48 hours of incubation at the temperature of 30° C., by the method of imprints for the ability of being grown on two media of the following composition: Medium I (mg/ml): glucose—20.0, $Na_2SO_4$—2.0, $K_2HPO_4$—1.0, $NH_4CL$—3.0, $NH_4NO_3$—1.0, $MgSO_4.7H_2$)—0.1, $MnSO_4.5H_2O$—$1\times10^{-4}$, $FeSO_4.7H_2O$—$1\times10^{-4}$, biotin—$5\times10^{-5}$, thiamine chloride—$1\times10^{-4}$, agar—agar—20.0, pH=7.4. The composition of medium 2 differs from that medium 1 in that it contains 100 μg/l of D-alanine. Mutants of *Brevibacterium flavum* AA1 and *Brevibacterium flavum* AA2 are selected among colonies incapable of being grown after 48 hours of incubation at the temperature of 30° C. on medium 1, but growing on medium 2.

The strains producing L-alanine according to the present invention, viz., *Corynebacterium glutamicum* AA41 and *Corynebacterium glutamicum* AA11 have the following morphological-and-cultural and physiological-and-biochemical features:

Cells oval, short, non-sporiferous. Gram positive. After 48 hours of incubation on a meat-peptone agar the colonies are round, glossy, creamy in colour; edges smooth, diameter of the colonies—2–3 mm.

Facultative anaerobics. Do not coagulate milk. Do not liquify gelatine. Ferment glucose and saccharose. Assimilate ammonium nitrogen and urea. Optimal growth at 30°–32° C. and at a pH of 7.2–7.8. Need thiamine for growth on minimal media.

The strains AA5 and AA6 do not differ, in their characteristics (except for their resistance against D,L-α-aminobutyric acid, auxotrophicity relative to D-alanine and L-alanine producing capacity), from the parental strain *Brevibacterium flavum* ATCC 14067.

The strains—producers of L-alanine according to the present invention—*Brevibacterium flavum* AA5 and *Brevibacterium flavum* AA6 have the following cultural-and-morphological characteristics:

Morphological features:

Cells oval, slightly extended of 1.7–2.5 μm length, nonsporiferous, immobile, gram-positive.

Cultural features

They form colonies in a meat-peptone agar on the 2-nd day of growing; 2 mm in diameter, round, smooth, of yellowish colour.

Scratch on a meat-peptone agar. On the 2-nd day the growth is moderate, the edge is even, the surface smooth, dense, glossy, of creamy-yellowish colour.

Growth on the injection on a meat-peptone agar. Moderate, mainly on the medium surface.

Glover's mineral medium with glucose. Needed for the growth are: biotin, thiamine and D-alanine. On the 2-nd day of the growth at 30° C. form colonies of 1 mm in diameter of light-creamy colour. Grown on potatoes and form a pigment with a yellowish shade. Do not liquify gelatin.

Relation to sources of carbon. They ferment glucose, saccharose, mannose, fructose, maltose; less actively ferment galactose, rhamnose, sorbose, sorbitol, ammonium and sodium salts of acetic acid, ethanol, do not ferment lactose.

Relation to sources of nitrogen. Assimilate ammonium sulphate and ammonium chloride, urea.

Optimal growth at 30°–32° C. and at a pH of 7.2–7.8.

The strain *Brevibacterium flavum* AA5 is prepared in the following manner.

The strain *Brevibacterium flavum* ATCC 14067 is grown in a meat-peptone broth at the temperature of 30° C. under aeration till the titre of $10^9$ cells/ml is reached. The cells are rinsed from the meat-peptone broth by centrifugation and resuspended in a citrate buffer with the pH of 5.5. The resulting suspension is added with N-methyl-N'-nitro-N-nitrosoguanidine to the final concentration of 300 µg/ml and subjected to incubation for 20 minutes at the temperature of 30° C. under aeration. Then the cells are rinsed from the mutagene with a cooled meat-peptone broth, transferred into test tubes with 10 ml of a meat-peptone broth, subjected to incubation for 18 hours at 30° C. and then inoculated onto the surface of medium No. 1 having the following composition (mg/ml): glucose—20, Na$_2$SO$_4$—2, K$_2$HPO$_4$—1, NH$_4$Cl—3, NH$_4$NO$_3$—1, MgSO$_4$.7-H$_2$O—0.1, MnSO$_4$.5H$_2$O—1×10$^{-4}$, FeSO$_4$.7-H$_2$O—1×10$^{-4}$, biotin—5×10$^{-5}$; thiamine chloride—1×10$^{-4}$, agar-agar—20, D,L —α—aminobutyric acid—30, pH=7.4. The colonies grown on this medium No. 1 after 4–5 days of incubation at the temperature of 30° C. are cleaned and tested for their alanine-producing capacity. One of the thus-selected mutants producing increased amounts of D,L-alanine is again subjected to mutagenesis with N-methyl-N'nitro-N-nitrosoguanidine and mutants necessitating D-alanine for their growth are chosen. The strain *Brevibacterium flavum* AA5 producing L-alanine is one of the thus-selected mutants.

The strain *Brevibacterium flavum* AA6 is prepared in the following manner.

The strain *Brevibacterium flavum* ATCC 14067 is subjected to mutagenesis with N-methyl-N'-nitro-N-nitrosoguanidine and a mutant necessitating D-alanine for its growth is selected. The resulting mutant needing D-alanine for its growth is again subjected to mutagenesis with N-methyl-N'-nitro-N-nitrosoguanidine and mutants resistant against D,L-α-aminobutyric acid are selected in a manner similar to that described for the preparation of the strain *Brevibacterium flavum* AA5, but into the composition of medium No. 1 D-alanine is also incorporated in the concentration of 0.1 mg/ml. One of the thus-selected mutants producing increased amounts of L-alanine is denoted as *Brevibacterium flavum* AA6.

The strains *Corynebacterium glutamicum* AA11 and *Corynebacterium glutamicum* AA41 are prepared from the strain Corynebacterium glutamicum ATCC 13032 by selection techniques similar to those specified hereinbefore for the preparation of strains *Brevibacterium flavum* AA1 and *Brevibacterium flavum* AA2 from the strain *Brevibacterium flavum* ATCC 14067.

The distinctive features of the strains according to the present invention in comparison with the respective parental strains Brevibacterium flavum ATCC 14067 and Corynebacterium glutamicum 13032 are shown in the following Table.

TABLE

| No | STRAIN | Ability for growing on a medium | | | Ability for accumulation of D-alanine and L-alanine in the medium, % | |
|---|---|---|---|---|---|---|
| | | Without D-alanine | With D-alanine (100 µg/ml) | With-D-alanine (100 µg/ml) and D,L-α-aminobutyric acid (30 mg/ml) | D-Alanine | L-Alanine |
| 1 | 2 | 3 | 4 | 5 | 6 | 7 |
| 1 | *Brevibacterium flavum* ATCC14067 | + | + | − | 45 | 55 |
| 2 | *Brevibacterium flavum* AA1 | − | + | − | 0 | 100 |
| 3 | *Brevibacterium flavum* AA2 | − | + | − | 0 | 100 |
| 4 | *Brevibacterium flavum* AA5 | − | + | + | 0 | 100 |
| 5 | *Brevibacterium flavum* AA6 | − | + | + | 0 | 100 |
| 6 | *Corynebacterium glutamicum* ATCC 13032 | + | + | − | 48 | 52 |
| 7 | *Corynebacterium glutamicum* AA11 | − | + | − | 0 | 100 |
| 8 | *Corynebacterium glutamicum* AA41 | − | + | − | 0 | 100 |

To determine the demand for D-alanine for growing the strains mentioned in the above Table, suspensions of these strains are applied by means of a loop onto the surface of media No 1 and No 2 (their composition is specified hereinbefore) and subjected to incubation for 40 hours at the temperature of 30° C. The appearance of growth is denoted by the sign "+" and its absence—by the sign "−".

The strains AA1, AA2, AA5, AA6, AA11, and AA41, in contrast to the parental strains ATCC 14067 and ATCC 13032 do not grow on medium No. 1.

Strains AA5 and AA6 unlike the rest of the strains specified in the Table, are capable of growing on a medium whose composition is similar to that of medium No. 2, the difference being in that it also comprises 30 mg/ml of D,L-α-aminobutyric acid.

To determine the ability of the strains to synthesize D-and L-alanine stereoisomers, suspensions of these strains are charged into test-tubes containing 5 ml of a sterilized medium of the following composition (g/l): glucose—50%, $(NH_4)_2SO_4$—30,0, $KH_2PO_4$—3.0, $MgSO_4.7H_2O$—1.0, D-alanine—0.1, $FeSO_4.7H_2O$—0.01, $MnSO_4.5H_2O$—0.01, biotin—0.002, thiamine bromide—0.00005, $CaCO_3$—30.0 at such a rate that the concentration of the microorganisms be equal to $10_7$ cells/ml. The test tubes are subjected to incubation under shaking at the temperature of 30° C. for 40 hours. In the resulting cultural liquid the content of D,L-alanine (the total content of both D- and L-forms of alanine) is determined by the method of paper chromatography and by dyeing with ninhydrin, or by means of an aminoacid analyzer. The content of D-alanine is determined by means of an enzyme of D-oxidase of aminoacids in a reaction mixture of the final volume of 0.4 ml containing: 8 milliunits of oxidase of D-aminoacids from swine kidneys, 0.2 ml of the test solution with the content of D-alanine of 0.1–0.5 mM, 33 mM of a pyrophosphate buffer with the pH of 8.3. The reaction is conducted at the temperature of 37° C. to achieve an equilibrium at which 93–95% of D-alanine are converted into pyruvate. The thus-formed pyruvate is determined spectrophotometrically at the wavelength of 440 nm. Then, on the basis of the measured values of the total content of D,L-alanine and D-alanine the percentage of D- and L-forms of alanine in the cultural liquids is calculated.

The data obtained are shown in the above Table. It follows from the Table that the strains AA1, AA2, AA5, AA6, AA11, and AA41, in contrast to the strains ATCC 14067 and ATCC 13032, are incapable of producing D-alanine.

The inoculation material of the producer strains for the subsequent fermentation can be prepared by any conventional method such as growing on the surface of nutrient media or in liquid nutrient media containing assimilable sources of carbon, nitrogen, inorganic salts and organic substances ensuring growth of the microorganisms.

The organic substances are represented by vitamins (biotin, thiamine) and other compounds including aminoacids, provided that they are indispensible for the growth of a particular producer strain.

As the nutrient fermentation medium for culturing mutants of microorganisms employed in the method according to the present invention use can be made of any nutrient media containing assimilable sources of carbon, nitrogen, inorganic salts, organic substances stimulating the growth of microorganisms and accumulation of L-alanine.

As the assimilable sources of carbon use can be made of such carbon sources as saccharose, glucose, fructose ,maltose, starch, starch hydrolyzate and molasses; polyhydric alcohols such as glycerol and sorbitol; organic acids such as formic acid, acetic acid, lactic acid, fumaric acid, maleic acid, propionic acid; alcohols such as methanol and ethanol. These sources of carbon can be used either separately or in any possible combination with one another in various weight proportions. The total amount of the agent–source of carbon can be introduced at the beginning of fermentation, or portion-wise during the fermentation process.

As the assimilable source of nitrogen used can be made of both organic and inorganic salts of ammonium such as ammonium sulphate, ammonium chloride, ammonium carbonate, ammonium acetate, ammonium nitrate, ammonium phosphate, ammonium lactate; ammonia, urea; various naturally-occurring nitrogen-containing compounds such as peptone, yeast hydrolyzate, meat extract, hydrolyzates of vegetable proteins.

As the inorganic salts use can be made of potassium phosphate, sodium phosphate, magnesium sulphate, sodium chloride, salts of iron, manganese and zinc, calcium carbonate.

As the organic substances required for the growth of the above-mentioned microorganisms use can be also made of thiamine, biotin or its substitutes, as well as aminoacids, provided that they are indispensible for the growth of the microorganisms. When the organic substances are present in sufficient amounts in the composition of the other components of the nutrient medium, there is no necessity in adding the organic substances in their pure form.

Accumulation of L-alanine occurs upon culturing of the abovespecified microorganisms at a temperature within the range of from 20° to 37° C. and at a pH value ranging from 6.5 to 9.0.

The appearance of L-alanine is observed 6–10 hours after the beginning of the fermentation. However, the maximum level of accumulation of L-alanine in the cultural liquid is reached as a result of a full consumption of the source of carbon and energy (after 32 hours and over depending on the used concentration of the carbon source and energy).

The content of L-alanine in the cultural liquid is determined by means of the method of paper chromatography and dyeing with ninhydrin, or by means of an aminoacid analyzer.

The accumulated L-alanine can be recovered from the cultural liquid by any conventional method such as the removal of microorganisms and other insoluble particles by centrifugation or filtration, adsorption of L-alanine on ion-exchange resins, followed by elution, concentration and crystallization of L-alanine.

EXAMPLE 1

Inoculation material of the strain Brevibacterium flavum AA2 is prepared by growing microorganisms in test tubes on the surface of a slant meat-peptone broth, containing 15 g/l of agar-agar and 100 m/l of D-alanine, during 22 hours at 30° C. and subsequent washing-off of the microorganisms with a sterile physiological solution (the concentration of the microorganisms in the resulting suspension is $10^9$ cells/ml).

Into each of 250 ml fermentation flasks there are poured aseptically 10 ml of a sterilized fermentation medium of the following composition (g/l): molasses—200.0 (as calculated for sugar, 100), hydrolysate of yeast biomass—120.0, $CaCO_3$—30.0, pH —7.5. Charged into the flasks is also 0.5 µl of an inoculation material of the strain *Brevibacterium flavum* AA2 and subjected to incubation under shaking (170 (rpm) for 72 hours at 30° C. The content of L-alanine in the cultural liquid obtained on completion of the fermentation is 5.1 g/l. 250 ml of the resulting cultural liquid of the strain *Brevibacterium flavum* AA2, containing 5.1 g of L-alanine, are centrifugated (500 rpm for 20 minutes) to remove the bacteria and other insoluble particles. The supernatant thus obtained is passed through a column with an ion-exchange resin in the $NH_4^+$ form from top downwards at a rate of 0.6–0.7 volumes of solution per volume of the resin per hour. The column is washed with water and the adsorbed L-alanine is eluted with a 3.5% aqueous solution of ammonia. The resulting eluate is concentrated under vacuum, and L-alanine is crystallized at a temperature of 14°-16° C. for 4 hours. The crystals are separated from the solution by filtering through a paper filter and dried under vacuum. The yield of L-alanine is 3.3 g without taking into account its content in the mother liquor, the total yield from the content thereof in the cultural liquid thus being 65%. The product purity, in accordance with the paper chromatography data, is 77.4%.

EXAMPLE 2

Inoculation material of the strain *Brevibacterium flavum* AA1 is prepared under the conditions described in Example 1.

Into each of 250 ml fermentation flasks there are poured aseptically 10 ml of a sterilized fermentation medium of the following composition (g/l): molasses 200.0 (as calculated for sugar, 100) hydrolysate of yeast biomass—120.0, $CaCO_3$, pH 7.5.

Charged into the flasks is also 0.5 ml of an inoculation material of the strain *Brevibacterium flavum* AA1, prepared under conditions similar to those specified in Example 1 hereinbefore. The flasks are subjected to inoculation under shaking (70 r.p.m.) for 72 hours at the temperature of 30° C. The content of L-alanine in the culture liquid prepared upon completion of the fermentation is equal to 69 g/l.

EXAMPLE 3

Into each of 250 ml fermentation flasks there are aseptically poured 10 ml of a sterilized fermentation medium of the following composition (g/l): molasses—200.0 (100 —based on sugar), yeast biomass hydrolyzate—120.0, $CaCO_3$—30.0, pH—7.5.

Charged into the flasks are portions of 0.5 ml of an inoculation material of the strain *Corynebacterium glutamicum* AA11 prepared under the conditions similar to those specified in Example 1. The flasks are subjected to incubation under shaking (70 r.p.m.) for 72 hours at the temperature of 30° C. The content of L-alanine in the culture liquid prepared after completion of the fermentation is equal to 3.8 g/l.

EXAMPLE 4

Into each of 250 ml fermentation flasks there are aseptically poured 10 ml of a sterilized fermentation medium of the following composition (g/l): molasses—200.0 (100 as calculated for sugar), yeast biomass hydrolyzate—120.0, $CaCO_3$—30, pH=7.5.

Charged into each of the flasks is 0.5 ml of an inoculation material of the strain *Corynebacterium glutamicum* AA41 prepared under conditions similar to those of Example 1. The flasks are subject to inoculation under shaking (70 r.p.m.) for 72 hours at the temperature of 30° C. The content of L-alanine in the cultural liquid obtained on completion of the fermentation is equal to 6.4 g/l.

EXAMPLE 5

The process of fermentation is carried out under conditions similar to those described in Example 1 hereinbefore, using the strain *Brevibacterium flavum* AA1 as the strain producing L-alanine, except that use is made of a nutrient fermentation medium of the following composition (g/l): saccharose—100.0, $(NH_4)_2SO_4$—55.0, $KH_2PO_4$—3.0, $MgSO_4.7H_2O$—1.0, D-alanine—0.1, $FeSO_4.7H_2O$—0.01, $MnSO_4.5H_2O$—0.01, biotin—0.0002, thiamine bromide—0.00005, $CaCO_3$—50.0, pH=7.5.

The content of L-alanine in the culture liquid after incubation for 72 hours is equal to 17.6 g/l.

EXAMPLE 6

The process of fermentation is carried out under conditions similar to those described in Example 1, except that as the strain producing L-alanine use is made of the strain *Brevibacterium flavum* AA2 and the employed fermentation medium has the following composition (g/l): saccharose—100.0, $(NH_4)_2SO_4$—55/0, $KH_2PO_4$—3.0, $MgSO_4.7H_2O$—1.0, D-alanine—0.1, $FeSO_4.7H_2O$—0.01, $MnSO_4.5H_2O$—0.01, biotin—0.00002, thiamine bromide—0.00005, $CaCO_3$—50.0, pH=7.5.

The content of L-alanine in the culture liquid after 72 hours of incubation is equal to 20.4 g/l.

EXAMPLE 7

The process of fermentation is conducted under conditions similar to those described in Example 1, except that as the strain producing L-alanine use is made of the strain *Corynebacterium glutamicum* and the employed fermentation medium has the following composition (g/l): saccharose—100.0, $(NH_4)_2SO_4$—55.0, $KH_2PO_4$—3.0, $MgSO_4.7H_2O$—1.0, D-alanine—0.1, $FeSO_4.7H_2O$—0.1, $MnSO_4.5H_2O$—0.01, biotin—0.00002, thiamine bromide—0.00005, $CaCO_2$—50.0, pH—7.5.

The content of L-alanine in the culture liquid after 72 hours of incubation is 2.6 g/l.

EXAMPLE 8

The process of fermentation is conducted under conditions similar to those specified in Example 1 hereinbefore, except that as the strain producing L-alanine use is made of the strain *Corynebacterium glutamicum* AA41 and the employed fermentation medium has the following composition (g/l): saccharose—100.0, $(NH_4)_2SO_4$—55.0, $KH_2PO_4$—3.0, $MgSO_4.7H_2O$—1.0, D-alanine—0.1, $FeSO_4.7H_2O$—0.01, $MnSO_4.5H_2O$—0.01, biotin—0.0002, thiamine bromide—0.00005, $CaCO_3$—50.0, pH=7.5.

The content of L-alanine in the culture liquid after 72 hours of incubation is 5.1 g/l.

The content of L-alanine in the culture liquid after 72 hours of incubation is 5.1 g/l.

EXAMPLE 19

The process of fermentation is carried out under conditions similar to those of Example 5, except that as the strain producing L-alanine the strain *Brevibacterium flavum* AA5 is introduced into the flasks. The fermentation medium has the following composition (g/l): saccharose—120.0, $(NH_4)_2SO_4$—55.0, $KH_2PO_4$—3.0, $MgSO_4.7H_2O$—1.0, D-alanine—0.1, $FeSO_4.7H_2O$—0.01, $MnSO_4$—$5H_2O$—0.01, biotin—0.00002, thiamine bromide—0.00005, $CaCO_3$—50.0, pH=7.5.

The flasks are subjected to incubation under shaking for 72 hours at the temperature of 30° C. The content of L-alanine in the culture liquid obtained on completion of the fermentation is equal to 32.9 g/l.

EXAMPLE 10

The process of fermentation is carried out under conditions similar to those mentioned in Example 5, as the strain producing L-alanine use being made of the strain *Brevibacterium flavum* AA6.

The fermentation medium has the following composition (g/l): saccharose—120.0, (NH$_4$)$_2$SO$_4$—55.0, KH$_2$PO$_4$—3.0, MgSO$_4$.7H$_2$O—1.0, D-alanine—0.1, FeSO$_4$.7H$_2$O—0.01, MnSO$_4$.5H$_2$O—0.01, biotin—0 00002, thiamine bromide—0.00005, CaCO$_3$—50.0, pH=7.5.

The flasks are subjected to incubation under shaking for 72 hours at the temperature of 30° C. under shaking. The content of L-alanine in the culture liquid produced on completion of the fermentation is equal to 31.4 g/l.

EXAMPLE 11

The process of fermentation is carried out under conditions similar to those described in Example 5, use being made of the strain *Brevibacterium flavum* AA1 as the strain producing L-alanine. The fermentation medium has the following composition (g/l): saccharose—120.0, (NH$_4$)$_2$SO$_4$—55.0, KH$_2$PO$_4$—3.0, MgSO$_4$.7H$_2$O—1.0, D-alanine—0.1, FeSO$_4$.7H$_2$O—0.01, MnSO$_4$.5H$_2$O—0.01, biotin—0.00002, thiamine bromide—0.00005, CaCO$_3$—50.0, pH=7.5.

The flasks are subjected to incubation for 72 hours at the temperature of 30° C. under shaking.

The culture liquid obtained on completion of the fermentation is equal to 20.6 g/l.

EXAMPLE 12

The process of fermentation is conducted under conditions similar to those specified in Example 5. However, into each of the flasks 0.5 ml of an inoculation material of the strain *Brevibacterium flavum* AA5 is introduced which comprises a suspension obtained by washing-off from one-day agarized slants of a meat-peptone broth (concentration of the microorganisms is 10$^9$ cells/ml). The fermentation medium has the following composition (g/l): saccharose—150.0, (NH$_4$)$_2$SO$_4$—55.0, KH$_2$PO$_4$—3.0, MgSO$_4$—7H$_2$O—1.0, D-alanine—0.1, FeSO$_4$.7H$_2$O—0.01, MnSO$_4$.5H$_2$O—0.01, biotin —0.00002, thiamine bromide—0.00005; CaCO$_3$—50.0, pH=7.5.

The flasks are subjected to incubation for 96 hours at the temperature of 30° C. under shaking. The content of L-alanine in the culture liquid obtained on completion of the fermentation is equal to 43.8 g/l.

Purification of L-alanine from 250 ml of the cultural liquid the strain *Brevibacterium flavum* AA5 (the total content of L-alanine being 11 grams) is carried out under the conditions similar to those set forth in Example 1. The yield of the L-alanine without taking into account its content in the mother liquor is 7.3 g, the total yield thereof from its content in the cultural liquid thus being 67%. The purity of the product, according to the paper chromatography data, is 91.3%.

EXAMPLE 13

The process of fermentation is conducted under conditions similar to those of example 5 hereinbefore.

However, into each flask 0.5 ml of an inoculation material of the strain *Brevibacterium flavum* AA6 is introduced which comprises a suspension produced by washing-off from one-day agarized slants of a meat-peptone broth (concentration of the microorganisms is 10$^9$ cells/ml). The fermentation medium has the following composition (g/l) saccharose—150.0, (NH$_4$)$_2$SO$_4$—55.0, KH$_2$PO$_4$—3.0, MgSO$_4$.7H$_2$O —1.0, D-alanine—0.1, FeSO$_4$.7H$_2$O—0.01, MnSO$_4$.5H$_2$O—0.01, biotin —0 00002, thiamine bromide—0.00005, CaCO$_3$—50.0, pH=7.5.

The flasks are subjected to incubation for 96 hours at the temperature of 30° C. under shaking. The content of L-alanine in the culture liquid obtained on completion of the fermentation is equal to 42.3 g/l.

EXAMPLE 14

The process of fermentation is carried out under conditions similar to those specified in Example 5.

However, into each of the flasks 0.5 ml of an inoculation material of the strain *Brevibacterium flavum* AA1 is introduced which comprises a suspension obtained by washing-off from one-day agarized slants of meat-peptone broth (concentration of the microorganisms is 10$^9$ cells/ml). The fermentation broth has the following composition (g/l): saccharose—150.0, (NH$_4$)$_2$SO$_4$—55.0, KH$_2$PO$_4$—3.0, MgSO$_4$.7H$_2$O—1.0, D-alanine—0.1, FeSO$_4$.7H$_2$O—0.01, MnSO$_4$.5H$_2$O—0.01, biotin—0.00002, thiamine bromide—0.00005, CaCO$_3$—50.0, pH=7.5.

The flasks are subjected to incubation for 96 hours at the temperature of 30° C. under shaking. The content of L-alanine in the culture liquid obtained on completion of fermentation is 28.1 g/l.

INDUSTRIAL APPLICABILITY

The present invention is useful in medicine, chemical, food and tobacco industries.

What is claimed is:

1. A method for preparing optically pure L-alanine by culturing a microorganism of the genus *Brevibacterium* and *Corynebacterium* on a nutrient medium containing assimilable sources of carbon, nitrogen, inorganic salts and stimulants of growth of the microorganisms, said method comprising introducing into the nutrient medium a mutant selected from the group consisting of

*Brevibacterium Flavum* AA1;
*Brevibacterium Flavum* AA2;
*Brevibacterium Flavum* AA5;
*Brevibacterium Flavum* AA6;
*Corynebacterium glutamicum* AA41; and
*Corynebacterium glutamicum* AA11;

which mutants cannot grow in the absence of D-alanine and require D-alanine for their growth, allowing said L-alanine to accumulate in the culture liquid, and thereafter recovering said L-alanine.

2. A method according to claim 1, wherein said mutants are microorganisms belonging to the species *Brevibacterium flavum*:
   strain *Brevibacterium flavum* AA5 No. B-3991 and
   strain *Brevibacterium flavum* AA6 No. B-3992.

3. A method for preparing L-alanine by culturing a microorganism of the genus *Brevibacterium* and *Corynebacterium* on a nutrient medium containing assimilable sources of carbon, nitrogen, inorganic salts and stimulants of growth of the microorganisms, said method comprising introducing into the nutrient medium a mutant of a microorganism selected from the group consisting of microogranism of the genus Brevibacterium or Corynebacterium which require D-alanine for their growth, said L-alanine to accumulate in the culture liquid, and thereafter recovering said L-alanine.

4. A method according to claim 3, wherein said mutants are microorganisms belonging to the species *Brevibacterium flavum*:
   strain *Brevibacterium flavum* AA1 No. B-3061 and
   strain *Brevibacterium flavum* AA2 No. B-3062.

5. A method according to claim 3, wherein said mutants are microorganisms belonging to the genus Brevibacterium which are resistant to D,L-alpha-aminobutyric acid.

6. A method according to claim 3, wherein said mutants are microorganisms belonging to the species *Corynebacterium glutamicum;*
strain *Corynebacterium glutamicum* AA41 No. B-3321 and
strain *Corynebacterium glutamicum* AA11 No. B-3323.

* * * * *